United States Patent [19]

Hinchee et al.

[11] Patent Number: 5,569,834

[45] Date of Patent: Oct. 29, 1996

[54] METHOD FOR SOYBEAN TRANSFORMATION AND REGENERATION

[75] Inventors: Maud A. Hinchee, Manchester; Dannette Connor-Ward, Olivette, both of Mo.

[73] Assignee: Monsanto Company, St. Louis, Mo.

[21] Appl. No.: 388,642

[22] Filed: Feb. 14, 1995

Related U.S. Application Data

[62] Division of Ser. No. 156,611, Nov. 23, 1993, Pat. No. 5,416,011, which is a continuation of Ser. No. 18,347, Feb. 16, 1993, abandoned, which is a continuation of Ser. No. 223,147, Jul. 22, 1988, abandoned.

[51] Int. Cl.⁶ .................................................. A01H 4/00
[52] U.S. Cl. .................. 800/205; 800/250; 800/DIG. 26
[58] Field of Search ................................ 435/172.3, 240.4, 435/240.45, 240.48, 240.49, 240.51; 800/205, DIG. 26, 250

[56] References Cited

U.S. PATENT DOCUMENTS

| | | | |
|---|---|---|---|
| 4,769,061 | 9/1988 | Comai | 800/205 |
| 5,015,580 | 5/1991 | Christou et al. | 435/172.3 |
| 5,188,642 | 2/1993 | Shah et al. | 800/205 |

*Primary Examiner*—Che S. Chereskin
*Attorney, Agent, or Firm*—Lawrence M. Lavin, Jr.; Dennis R. Hoerner, Jr.

[57] ABSTRACT

A method for Agrobacterium-mediated transformation and regeneration of soybean is disclosed. The method utilizes a cotyledon explant which is prepared by first removing the hypocotyl and then tearing the two cotyledons apart at the cotyledonary node. The explant may be inoculated with either a smear of the disarmed Agrobacterium vector or of liquid culture of the bacterium.

2 Claims, 3 Drawing Sheets

5,569,834

METHOD FOR SOYBEAN TRANSFORMATION AND REGENERATION

This is a division of application Ser. No. 08/156,611, filed Nov. 23, 1993, now U.S. Pat. No. 5,416,011, which is a continuation of 08/018,347, filed Feb. 16, 1993, abandoned, which is a continuation of 07/223,147, filed Jul. 22, 1988, abandoned.

The present invention relates to plant cell transformation and regeneration into a differentiated transformed plant. More particularly, the invention relates to a method for transforming soybean (*Glycine max*) using Agrobacterium-mediated transformation of a plant tissue explant and subsequent regeneration of the transformed cells into a whole plant.

Soybean is grown on approximately 34 million hectares in the United States and Brazil. Unfortunately, only a few plant introductions have given rise to the major cultivars grown in the United States and, as a consequence, this narrow germplasm base has limited soybean breeding. Hence, modification of soybean using genetic engineering techniques would facilitate the development of new varieties with traits such as herbicide resistance, disease resistance such as virus resistance and seed quality improvement in a manner unattainable by traditional breeding methods or tissue-culture induced variation. Genes have been transferred to soybean protoplasts by electroporation of free DNA (Christou et al., 1987 and Lin et al., 1987). However, regeneration technology for soybean has not progressed to a state where regenerated plants can be produced from protoplasts. Soybean shoot organogenesis occurs from tissues such as cotyledonary nodes (Cheng et al., 1980; Wright et al., 1986; and BaNale et al., 1986) as well as primary leaves of seedlings (Wright et al., 1987). Somatic embryogenesis has been demonstrated from immature embryos and cotyledons of developing seeds (Ranch et al., 1985; Lazzeri et al., 1985; Ghazi et al., 1986; Barwale et al., 1986; and Hammat et al., 1987).

STATEMENT OF THE INVENTION

The present invention provides a method for transformation of soybean explants and regeneration of the transformed explant into a differentiated transformed plant.

In one aspect, the present invention embraces the discovery of a novel soybean explant which enables *Agrobacterium tumefaciens* mediated transformation of cells which are competent to regenerate into whole transformed plants. In another aspect the present invention embraces a method for transforming soybeans which comprises:

(a) preparing a cotyledon explant from a soybean seedling by:
  (i) removing the hypocotyl region by cutting just below the cotyledonary node,
  (ii) separating the two cotyledons at the cotyledonary node by tearing the cotyledons apart, and
  (iii) removing the epicotyl from the cotyledon to which it is attached,
(b) inserting a chimeric gene into the explant of part (a) by inoculation and co-cultivation of the explant with a disarmed *Agrobacterium tumefaciens* vector containing said chimeric gene;
(c) selecting transformed explant tissue, and
(d) regenerating a differentiated transformed plant from the transformed explant tissue of part (c).

In yet another aspect, the present invention embraces a method further comprising wounding the cotyledon explant prior to inoculation by making at least one cut in the petiole region (which includes the axillary bud) of the explant.

Transgenic soybean plants have been obtained within 3–4 months by a procedure which uses Agrobacterium-mediated DNA transfer. The transgenic nature of these $R_o$ plants was confirmed by expression of introduced traits (glucuronidase, GUS; neomycin phosphotransferase, NPTII; and/or a glyphosate tolerant EPSP synthase) in leaves and in progeny. Southern hybridization analysis of the progeny of one pMON9749 (GUS) plant showed segregation for the expected DNA fragments. The development of the preferred embodiment of the present soybean transformation protocol relied upon the variation of several parameters such as soybean cultivar, Agrobacterium strain, explant source, and antibiotic selection. Optimization of these parameters was facilitated by the use of the GUS histochemical marker, since the effect of different treatments could be assessed in tissues long before plantlets could be analyzed.

The cultivars which were used in the exemplary embodiments of the soybean transformation protocol provided hereinafter were those determined to be most susceptible to Agrobacterium transformation. This is important since soybean is a relatively poor host for Agrobacterium. It had previously been reported that only 2.5% of nearly 1000 soybean cultivars were susceptible to tumor induction by Agrobacterium (Wang et al., 1983). However, the transformation of soybean cells does not always result in the formation of a tumor (Faccioti et al., 1985). An in vitro screen to identify susceptible soybean genotypes was developed based on the ability of cultivars to produce kanamycin resistant callus after Agrobacterium transformation. The *A. tumefaciens* strain A208 carrying the disarmed nopaline plasmid pTiT37-SE (EPO Publ. No. 218,571) was the vector chosen for this screen since A208 is highly virulent on soybean (Byrne et al., 1987). The cultivars Delmar, Maple Presto and Peking produced significantly more kanamycin resistant callus than did other cultivars after transformation with *A. tumefaciens* strain pTiT37-SE::pMON273. The cultivar Peking had been previously identified as a genotype which was susceptible to Agrobacterium based on tumor formation (Owens et al., 1985; Byrne et al., 1987), and this cultivar's in vitro response to Agrobacterium correlated with its in vivo response.

The cotyledon regeneration system proved to be an excellent vehicle for the production of transgenic soybean plants. Shoot formation was rapid and prolific, and a large proportion of these shoots developed into fertile plants. In addition, this explant allowed Agrobacterium transformation to be targeted to regeneration competent tissue. Other regeneration systems for soybean such as cotyledonary node (Cheng et al., 1980; Wright et al., 1986; Barwale et al., 1986), primary leaf (Wright et al., 1987)and immature embryo (Ranch et al., 1985; Lazzeri et al., 1985; Ghazietal, 1986; Barwale et al., 1986; and Hammat et al., 1987) have not yet yielded transgenic plants via Agrobacterium-mediated transformation. In these systems, Agrobacterium transformation may be targeted to cells which do not readily regenerate. Transformation of protoplasts have been transformed by both Agrobacterium (Baldes et al., 1987) and electroporation of free DNA (Christou et al., 1987 and Lin et al., 1987). Unfortunately, plant regeneration from soybean protoplasts is not yet possible.

Selection of transformed tissue is most often accomplished in plant transformation by inserting an antibiotic resistant gene into the transformed tissue. Numerous antibiotics have been demonstrated to be effective in plant transformation including, but not limited to, gentamicin, kanamycin, hygromycin as well as methotrexate a non-antibiotic selection agent. For purposes of the present invention kanamycin is preferred. Kanamycin selection enriched for the transformed cell population and facilitated the production of transgenic soybean shoots. Visualization of GUS in transformed cells clearly demonstrated that soybean cells transformed with pMON9749 grew better with kanamycin than without. This selection aided in the production of transgenic shoots by allowing transformed cells to grow into tissues capable of initiating multicellular shoot primordia. Kanamycin resistance has proven to be a nearly universal selectable marker for transformed plant cells since it has been effective in the transformation of plant species as diverse as oil seed rape (Fry et al., 1987), lettuce (Michelmore et al., 1987) and corn (Rhodes et al., 1988).

Construction of *Agrobacterium tumefaciens* mediated transformation vectors is well known in the art, see for example Rogers et al., 1986; Rogers et al., 1987a; Rogers et al., 1987b; and Deblaere et al., 1987. The Agrobacterium-mediated transformation vectors can be used to insert a selected chimeric plant gene into an explant susceptible to infection by the Agrobacterium host.

Briefly, the gene comprises a promoter, structural coding sequence and a 3' polyadenylation signal. Promoters which are known or found to cause transcription of the EPSPS gene in plant cells can be used in the present invention. Such promoters may be obtained from plants or viruses and include, but are not necessarily limited to, the 35S and 19S promoters of cauliflower mosaic virus and promoters isolated from plant genes such as EPSPS, ssRUBISCO genes and promoters obtained from T-DNA genes of *Agrobacterium tumefaciens* such as nopaline and mannopine synthases. The particular promoter selected should be capable of causing sufficient expression to result in the desired phenotypic trait. The RNA produced by the gene also contains a 5' non-translated leader sequence. This sequence may be derived from any gene and may be specifically modified so as to increase translation of the mRNA. The 5' non-translated regions may be derived from viral RNAs, other suitable eukaryotic genes or a synthetic gene sequence. It may be part of the 5' end of the non-translated region of the structural coding sequence for the encoded polypeptide or derived from an unrelated promoter or coding sequence as discussed above. The 3' non-translated region contains a polyadenylation signal which functions in plants to cause the addition of polyadenylate nucleotides to the 3' end of the mRNA. In cases where the structural coding sequence is derived from a plant source one can use the 3' non-translated region naturally associated with the particular plant gene. Examples of other suitable 3' regions are the 3'transcribed, non-translated regions containing the polyadenylation signal of the nopaline synthase (NOS) gene of the Agrobacterium tumor-inducing (Ti) plasmid or the conglycinin (7S) storage protein gene.

The genetic modification of soybean through biotechnology has great agricultural value. Soybean is a major food and feed source which is grown on more acres worldwide than any other dicotyledonous crop. The limited genetic base in domestic soybean varieties has limited the power of traditional breeding methods to develop varieties with improved or value-added traits. The development of herbicide resistant soybean cultivars would provide simpler and more effective weed control in soybean fields. The glyphosate resistant soybean plant produced using this soybean transformation protocol is an example of the speed in which new agronomic traits can now be introduced into soybean cultivars.

DETAILED DESCRIPTION OF THE PREFERRED EMBODIMENTS

Figure 1:
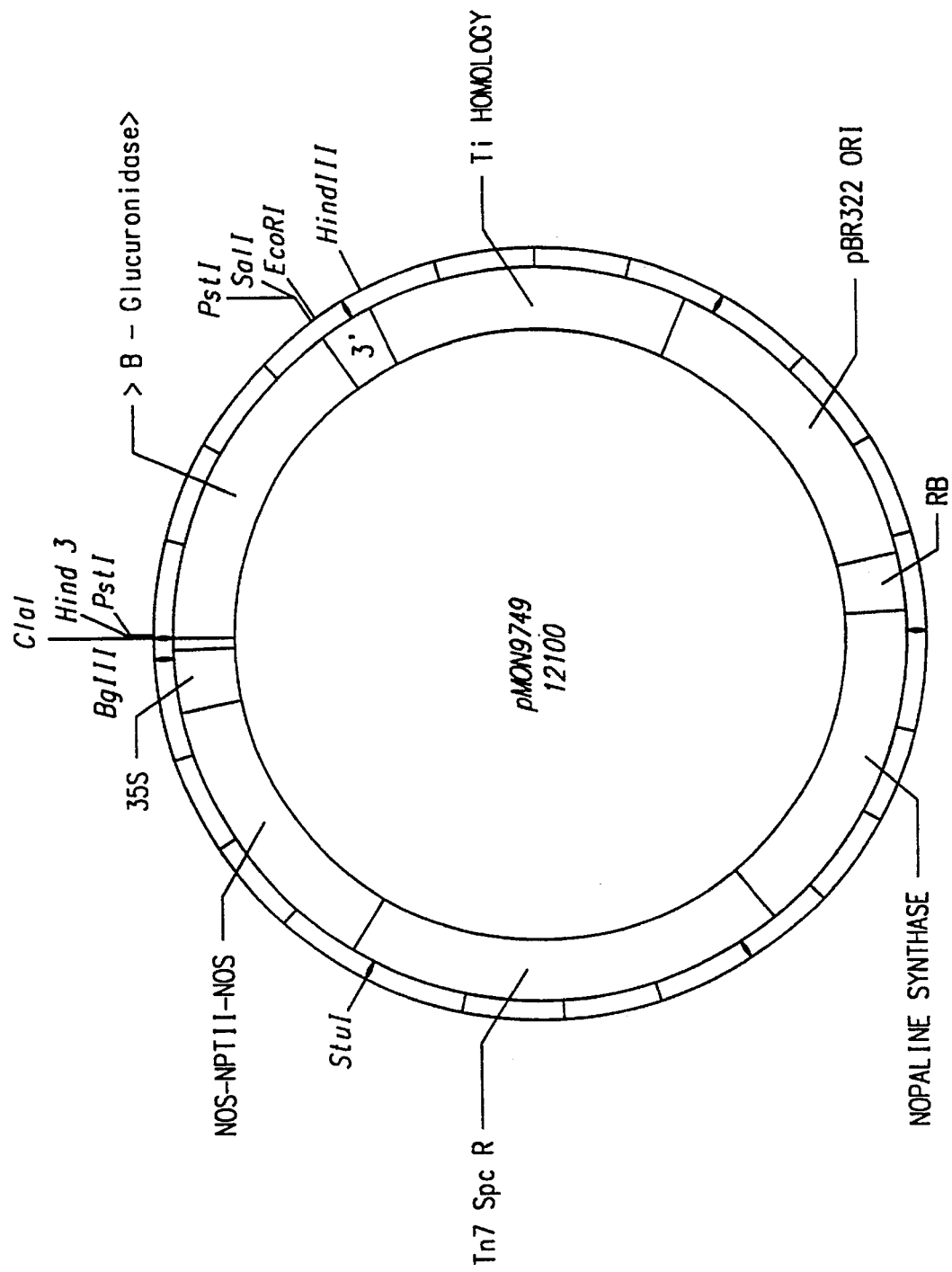
FIG. 1 shows a map of plasmid pMON9749.

Numerous soybean cultivars, chosen for their relative diversity, were screened for their in vitro response to *A. tumefaciens* mediated transformation. All cultivars grew callus on MS NAA/K medium. This medium contains MS salts and organics (Murashige and Skoog, 1962) with 2.15 mg/l kinetin and 4.68 mg/l napthalene acetic acid (NAA). Therefore, this medium was chosen for use in an in vitro screen for *A. tumefaciens* susceptibility based on the production of antibiotic resistant callus. The susceptibility was determined by scoring the number of soybean hypocotyls which were capable of producing callus on MS NAA/K medium containing 100 mg/l kanamycin after inoculation and co-culture with *A. tumefaciens* pTiT37-SE::pMON273 (Rogers et al., 1987 and Sanders et al., 1987). The intermediate plasmid pMON273, which contains a chimeric neomycin phosphotransferase II (NPTII) gene with the cauliflower mosaic virus (CaMV) 35S promoter and the nopaline synthase (NOS) 3' polyadenylation signal, confers resistance to the antibiotic kanamycin. Hypocotyl explants transformed with *A. tumefaciens* pTiT37-SE::pMON120 (Fraley et al., 1985), a construct which does not confer kanamycin resistance, never callused on MS NAA/K medium containing kanamycin.

Soybean seeds of about one hundred different soybean cultivars and plant introductions were aseptically germinated for 4 days on 0.8% Difco purified agar. Hypocotyls were cut into 5 mm segments, and inoculated by smearing the cut ends of the hypocotyls with *A. tumefaciens* pTiT37-SE::pMON273. The hypocotyl segments were co-cultured with the Agrobacterium vector for two days on 1/10 SH (Shenk and Hildebrandt) medium (1/10 the major and minor salts of SH, Gainborg et al., 1968) prior to being placed on MS NAA/K medium containing 500 mg/l carbenicillin with or without 100 mg/l kanamycin. MS NAA/K medium is composed of MS salts and organics (Schenk et al., 1972) with 2.15 mg/l kinetin and 4.68 mg/l napthalene acetic acid (NAA). Each cultivar sample was represented by 20–40 segments. The hypocotyl segments remained on MS NAA/K for 4 weeks prior to scoring. The number of hypocotyls which produced callus were counted as well as the number of independent calli per explant.

The callusing responses for seven cultivars of the over one hundred cultivars screened are shown in Table I below in order to show the range in cultivar response. Specifically, Table I shows the callusing response of soybean hypocotyl segments after inoculation and co-culture with *A. tumefaciens* pTiT37SE::pMON273 and subsequent culture on MS NAA/K medium containing 100 mg/l kanamycin.

TABLE I

| Cultivar | Total Number | Number Callusing | Number Calli |
|---|---|---|---|
| Maple Presto | 35 | 13 | 22 |
| Peking | 35 | 13 | 19 |
| Delmar | 30 | 10 | 18 |
| PI 181537 | 35 | 7 | 10 |
| Cutler 71 | 35 | 5 | 5 |
| Altona | 28 | 3 | 5 |
| Hartz 5370 | 18 | 0 | 0 |

The cultivars Maple Presto and Peking were identified as the most responsive cultivars and were used in subsequent transformation experiments. Although some cultivars did not exhibit a callusing response in the above screen (e.g. Hartz 5370), this observation is believed to be the result of low frequency. There is no expectancy that these cultivars could not be transformed and regenerated by the method described herein albeit probably at a lower frequency than the more responsive cultivars.

Cotyledon explants did not demonstrate efficient selection for kanamycin resistant callus as did the smaller hypocotyl explants. To determine the efficacy of Agrobacterium transformation of cotyledon explants and to determine if transformation could be targeted to the tissues competent to regenerate, the β-glucuronidase (GUS) gene was used as a histochemical marker (Jefferson, 1987). The vector pMON9749 (FIG. 1) is an integrating plant transformation vector in which the GUS gene is driven by the 35S promoter of cauliflower mosaic virus and contains the NOS 3'polyadenylation signal. pMON9749 was constructed as follows: A HindIII/EcoRI fragment of pRAJ260 (Jefferson et al., 1986) containing the GUS coding sequence was inserted into HindIII/EcoRI digested Bluescript KS+ (Stratagene, La Jolla, Calif.) resulting in pMON9948. The gene was removed from pMON9948 on a ClaI/EcoRI fragment and was inserted into pMON316 (Rogers et al., 1987b) that had been digested with the same enzymes. NOS-NPTII-NOS, a marker allowing for selection of kanamycin resistant plant cells; Tn7 Spec R, bacterial spectinomycin resistance gene from transposon Tn7; RB, the right border of the pTiT37 T-DNA; 35S, the 35S promoter from cauliflower mosaic virus; 3', the poly-(A) addition region of the nopaline synthase gene.

The vector was integrated into the disarmed Ti plasmid A. tumefaciens pTiT37-SE (EPO Publ. No. 218,571). Soybean cotyledon explants were inoculated with A. tumefaciens pTiT37-SE::pMON9749 and assayed for GUS activity after 3 weeks of culture on B₅BA medium containing kanamycin 200–300 mg/l. BsBA medium is composed of Bs salts (Gamborg et al., 1968), 20mg/l sucrose, 1.15 mg/l benzyladenine (BA), 8 g/l Difco purified agar at pH 5.8 prior to autoclaving. Transformed cells were identified after the hydrolytic action of the GUS enzyme converted the substrate 5-bromo-4-chloro-3-indolyl glucuronide (X-Gluc) into an insoluble blue precipitate in the cell cytoplasm (Jefferson, 1987). In free hand sections of the cotyledons, multiple GUS-positive callus sectors were identified in callus associated with the excision wound site. Some of these GUS-positive callus sectors were observed in the regeneration competent region of cotyledons adjacent to an incipient shoot primordium. The utility of the cotyledon explant in targeting Agrobacterium-mediated transformation to the regenerating cell population was more clearly demonstrated when several GUS positive shoot primordia were found. Similar shoot primordia and callus on cotyledons transformed with the plasmid pMON200 (Fraley et al., 1985) without the GUS gene did not react positively after the X-Gluc reaction. Utilizing the GUS analysis significantly sped up the development of the cotyledon transformation protocol, inasmuch as evidence for shoot transformation could be obtained several months before regenerated plants could be analyzed.

Briefly, in an exemplary embodiment the method of the present invention comprises sterilizing the seeds of a selected soybean cultivar and then germinating the sterilized seed to provide explant material. The prepared cotyledonary explant is inoculated with the A. tumefaciens transformation vector carrying the desired plant gene and a suitable selectable marker such as neomycin phosphotransferase II. The transformed cells are then selected under the appropriate antibiotic pressure. The surviving explants are then moved to shoot induction medium. Shoots are then transferred to root induction medium to produce a regenerated plant.

Seed Sterilization

The seeds are placed in a suitable sized flask (500 ml). The seeds are washed in a dilute aqueous detergent solution for about five minutes. The seeds are then washed 5 or 6 times with distilled water. The seeds are then alcohol washed with 70 wt % ethanol for about 1–2 minutes with occasional shaking. The ethanol is decanted and about 200 ml of 50% Chlorox (5.25% sodium hypochlorite) containing about one drop Tween 20 is added with occasional agitation. After 5–15 minutes the Chlorox solution is decanted and the seeds rinsed with sterile distilled water about 5 times or until there is no suds remaining. Enough sterile distilled water is added to cover the seeds along with a fungicide following the manufacturer's directions. The flask is gently shaken a few times and the seeds are soaked for about one hour. The fungicide solution is removed and the seeds stored in a dry, sterile petri dish.

Seed Germination

The sterile seeds of the selected soybean cultivar are germinated in petri dishes (100×25 mm) containing B₅O medium. B₅O medium is the same as B₅BA medium but without the benzyladenine. The seeds are simply laid on top of the medium. The plates are wrapped with parafilm or placed in plastic bags. The seeds are maintained under an environment of 16 hours light/8 hours dark, 27° C. for 4–5 days.

A. tumefaciens Preparation

The A. tumefaciens cells containing the selected transformation vector are grown in fresh LBSCCK medium about 2–5 days before use. The cells are grown at 25° C. LBSCCK consists of Luria Broth medium (either solid or liquid) with 50 mg/l spectinomycin, 50 mg/l streptomycin, 25 mg/l chloramphenical and 50 mg/l kanamycin. Luria Broth liquid medium consists of tryptone, 10 grams/l; yeast extract, 5 grams/l; sodium chloride, 10 grams/l at pH 7.0. Luria Broth solid consists of Luria Broth liquid with 15 grams/l Bacto Agar.

In the case of liquid culture a loopful of bacteria is added to 2 mls of LBSCCK medium two days prior to use. The next 2 ml of fresh medium is inoculated with 100–200 μl of the previous culture. For explant inoculation the next day the cells are spun down, washed with SHO medium and resuspended in an equal volume of SHO medium. For liquid inoculation about 10–16 ml of culture is preferably used per 10 cotyledon explants. In the case of smear inoculation preferably one plate of *A. tumefaciens* cells are used per 40 cotyledonary explant.

Explant Preparation/Inoculation

Figure 3A:
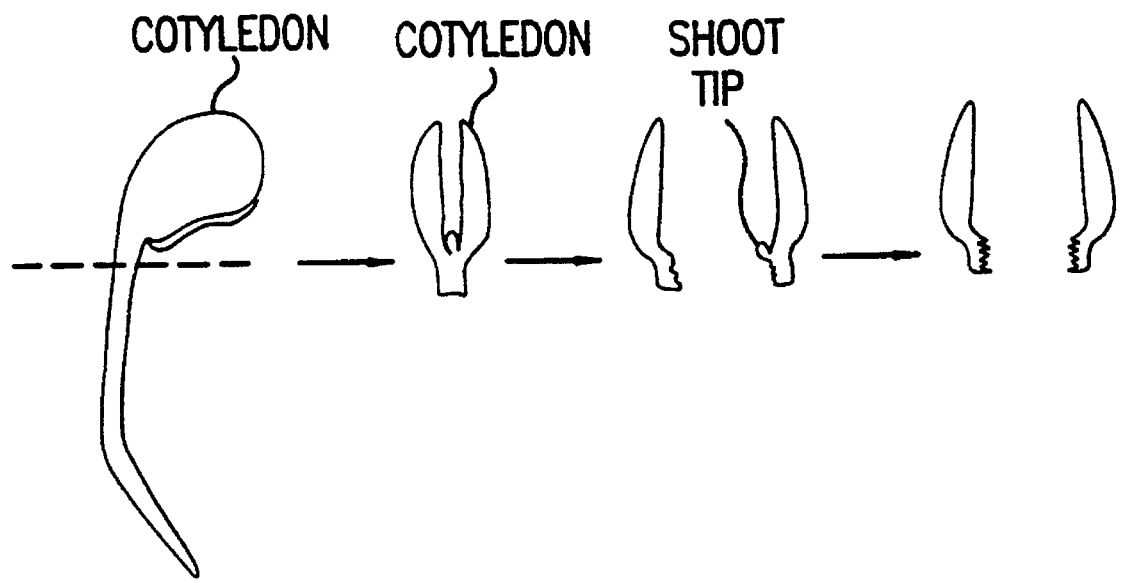
FIG. 3A shows the preparation of a soybean explant in accordance with the present invention.
Figure 3B:
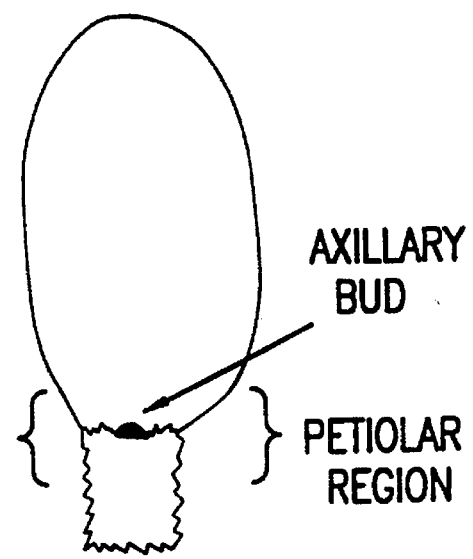
FIG. 3B shows area for inoculation.

Referring to FIG. 3, the cotyledon explant is prepared in the following manner. The seedlings are cut off about 3 mm below the cotyledons and put into a sterile empty plate. A small cut is made between the two cotyledons using straight forceps and a scalpel blade, and then the two cotyledons are ripped apart. The epicotyl is removed with forceps. The cotyledons are wounded by making 5–7 slight horizontal cuts in the petiole region (including the axillary bud area), one should be careful not to cut through the entire cotyledon. After preparing the explant as described above, it is put into the 1/10SHO plate (SH medium without hormones, containing +e,fra 200+ee μM Acetosyringone), preferably with the cotyledon positioned adaxial side up.

The end of the straight edge of the bacterial loop is rubbed across the surface of the bacterial plate a few times. The loop is carefully smeared in the axillary bud area of the wounded cotyledon. This procedure is repeated for each cotyledon, keeping the cover closed on the 1/10 SHO plate as much as possible. In the case of liquid inoculation, the explants are soaked in the bacteria solution for about one-half hour, blotted onto sterile filter paper and transferred to 1/10 SHO plates. It has been found that in many cases higher frequencies are obtained if the part of the explant away from the petiole is dug into the medium at a slant so the petiole is not in contact with the surface of the medium. Plates are wrapped with parafilm 12 cm by 5 cm folded in thirds, and put in the same percival as the germinated seeds were in. Transfer in 3–4 days.

Kanamycin Selection

Cotyledons are moved to a dish containing $B_5$–2.5–10 μM BA with 500 mg/l carbenicillin and 100 mg/l cefotaximine and 250 mg/l kanamycin. Cotyledons explant are put adaxial side in contact with the medium, without digging them into the medium. The inoculated cotyledons are maintained at 25° C. under a photoperiod of 16:8 (cool white fluorescent light at 40 uEn/s).

After four weeks all cotyledons are moved to $B_5O$ with 500 mg/l carbenicillen and 100 mg/l cefotaxime and 250 mg/l kanamycin. The petiole is preferably dug into the medium so the regenerating shoots are in contact with the medium. The cotyledon may be sideways or sticking up in the air. The plates are wrapped in parafilm. Explants producing shoots are subcultured every 4 weeks into fresh $B_5O$ medium. Cotyledon tissue that becomes necrotic is removed upon subculturing.

Root Induction/Plantlet Formation

Elongating shoots (1–2 inches) were removed and placed on ½ $B_5O$ medium (half the major and minor salts of $B_5O$ medium) in capped glass vials or in sterile 50 ml disposable plastic centrifuge tubes. Plantlets (rooted shoots) were moved to vermiculite in 2 inch pots after several new leaves had been produced. These plantlets were placed in a plastic container in which the lid was gradually opened to harden them off prior to growing in the greenhouse. Plantlets which had produced new leaves after hardening off were transplanted into soil and grown in the greenhouse for flowering and seed set.

EXAMPLE 1

Transgenic soybean plants which express β-glucoronidase were produced from explants of cultivars Peking and Maple Presto prepared in the manner described above. Cotyledon explants were prepared from seedlings obtained from germinated sterile seeds. The explant was inoculated with a smear of *A. tumefaciens* 208 containing pTiT37-SE::pMON9749. Plasmid pMON9749 (FIG. 1) contains the β-glucuronidase plant gene (CaMV35S/β-glucuronidase/NOS3') as well as the selectable neomycin phosphotransferase marker gene (NOS/NPTII/NOS). Transformed explant tissue was selected on media containing 200–300 mg/l kanamycin. Shoots from kanamycin resistant tissue were rooted and plantlets obtained.

Table II below lists results from three experiments involving transformation using pMON9749. Plantlets were determined to be transgenic by three different assays. Transgenic pMON9749 plants had leaves which were positive in the GUS histochemical reaction and the NPTII dot blot assay in addition to producing callus on MS19 medium containing 100 mg/l kanamycin.

β-glucuronidase (GUS) enzyme activity was located histochemically in unfixed free hand sections as described by Jefferson, 1987. After the histochemical reaction was complete, the sections were fixed in FAA for 1 day and cleared in 70% ethanol. The presence of nopaline was assayed by paper electrophoresis, Murashige and Skoog, 1962. Neomycin phosphotransferase II (NPTII) activity was determined by the dot blot procedure described by McDonnell et al., 987. Kanamycin resistance was assayed by the ability of leaf tissue to produce callus on MS19 medium containing 500 mg/l carbenicillin, 100 mg/l cefotaxime and 100 mg/l kanamycin. MS19 medium is composed of MS salts and organics with 2 mg/l BA and 0.5 mg/l NAA. Whole or cut leaflets were placed on the medium, and if callusing occurred within 4 weeks, they were scored as resistant. Nontransgenic leaf tissue failed to callus on this medium.

TABLE II

| Construct | Number Regenerating Total | Number of Plantlets | Number Transgenic |
| --- | --- | --- | --- |
| 9749 | 7/43 | 6 | 1[b] |
| 9749[a] | 6/130 | 13 | 1 |
| 9749 | 18/88 | 6 | 2 |

[a]This experiment utilized the cultivar Maple Presto
[b]Progeny analysis, infra.

EXAMPLE 2

Figure 2:
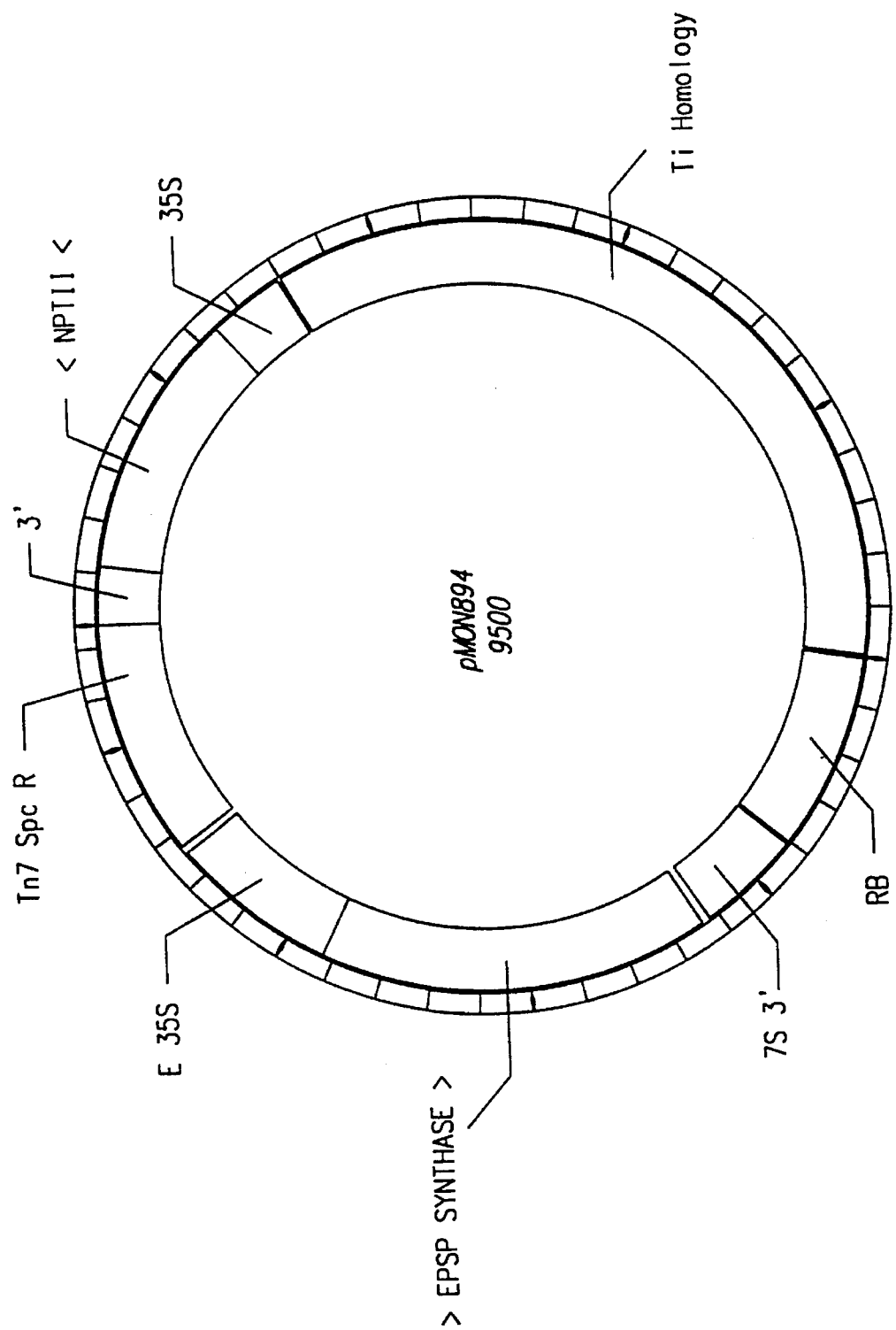
FIG. 2 shows a map of plasmid pMON894.

Transgenic soybean plants which express a mutant petunia 5-enolpyruvylshikimatephosphate synthase (EPSP synthase) tolerant toward glyphosate herbicide were produced from explants of the cultivar Peking in the manner described above. Construction of mutant EPSP synthase plant genes is described in commonly assigned U.S. patent applications Ser. No. 879,814, filed Jul. 7, 1986 and Ser. No. 179,245, filed Apr. 22, 1988, the disclosures of which are incorporated by reference herein. Cotyledon explants were prepared from seedlings obtained from germinated sterile seeds. The explant was inoculated with a smear of *A. tumefaciens* 208 containing pTiT37-SE::pMON894. Plasmid pMON894 (FIG. 2 contains the mutant petunia EPSP synthase gene, CaMV35S/Mutant petunia CTP/EPSPS/NOS3', as well as the selectable neomycin phosphotransferase II marker gene (NOS/NPTII/NOS). Transformed explant tissue was selected on medium containing 200–300 mg/l kanamycin. Shoots from kanamycin resistant tissue rooted and plants obtained. Table III below lists results obtained from three experiments involving the transformation of the Peking cultivar using pMON894. Transgenic pMON894 plants were positive in the NPTII dot blot assay, produced callus on MS19 medium containing 100 mg/l kanamycin and produced leaves which callused on MS19 medium containing 1.0 mM glyphosate.

TABLE III

| Construct | Number Regenerating Total | Number of Plantlets | Number Transgenic |
|---|---|---|---|
| 894 | 21/242 | 35 | 1 |
| 894 | 43/247 | 13 | 1[b] |
| 894 | 194/650 | 55 | 2 |

[b]Progeny analysis, infra.

Leaves of a transgenic soybean plant containing pMON894 displayed a higher level (4-fold) of EPSP synthase activity over that of wild type control leaves (Table IV). In addition, the EPSP synthase activity of the transgenic plant was unaffected by 0.5 mM glyphosate. Under these conditions, there is a complete inhibition of the endogenous EPSP synthase activity.

TABLE IV

| | EPSP Synthase Specific Activity[1] | |
|---|---|---|
| Plant | 0 mM | 0.5 mM Glyphosate |
| Wild Type | 7 | 0 |
| pMON894 | 30 | 30 |

[1]Expression of a petunia mutant EPSP synthase CDNA in a transgenic soybean plant leaf. EPSP synthase activity is expressed as the specific activity (nmol of EPSP formed/min mg/protein). Enzyme assays were performed in the presence of 0.5 mM glyphosate in order to completely inhibit the endogenous EPSP synthase activity and measure the mutant EPSP synthase activity resulting from the gene in pMON894.

Analysis of Transgenic Progeny

Of 14 selfed $R_1$ progeny from a pMON9749 transgenic soybean plant, 11 co-segregated for GUS and NPT activity. This is approximately a 3:1 segregation ratio indicating the presence of a single active T-DNA locus. Southern analysis confirmed that these progeny plants contained the inserted DNA fragment necessary to confer these genetic traits. Southern hybridization was performed on 6 of the $R_1$ progeny to assay for the presence and copy number of pMON9749 T-DNA in the plants. Two of the progeny analyzed were negative for GUS and NPTII, the other four were positive. Genomic DNA digested with HindIII was hybridized with a labeled pMON9749 probe. The four $R_1$ plants that were enzyme positive showed strong hybridization with the probe at a level consistent with one or a few copies of the T-DNA. All of the hybridizing plants showed the same pattern of putative T-DNA junction fragments indicating that there are no silent copies of the T-DNA segregating independently of the active copy. The junction fragment pattern is consistent with a single site of T-DNA insertion. This positive hybridization result and the correlation between enzyme activity and T-DNA in the $R_1$ progeny are evidence that this pMON9749 transgenic soybean plant was generated by the expected Agrobacterium-mediated events. A pMON894 plant also produced progeny which co-segregated in a 3:1 ratio for kanamycin resistance and glyphosate tolerance.

REFERENCES

Baldes, R., Moos, M. and Geider, K., 1987. "Transformation of Soybean Protoplasts from Permanent Suspension Cultures by Cocultivation with Cells of *Agrobacterium tumefaciens.*" *Plant Mol. Biol.* 9:135–145.

Barwale, U. B., Meyer, M. M. Jr. and Widholm, J. M., 986. "Screening of *Glycine max* and *Glycine soja* Genotypes for Multiple Shoot Formation at the Cotyledonary Node" *Theor. Appl. Genet.* 72:423–428.

Barwale, U. B., Kerns, H. R. and Widholm, J. M., 1986. "Plant Regeneration from Callus Cultures of Several Soybean Genotypes via Embryogenesis and Organogenesis" *Planta* 167:473–481.

Byrne, M. C., McDonnell, R. E., Wright, M. S. and Carnes, M. G., 1987. "Strain and Cultivar Specificity in the Agrobacterium-soybean Interaction."*Plant Cell Tissue and Organ Culture* 8:3–15.

Cheng, T-Y., Saka, H and Voqui-Dinh, T. H., 1980. "Plant Regeneration from Soybean Cotyledonary Node Segments in Culture." *Plant Science Letters* 19:91–99.

Christou, P., Murphy, J. E. and Swain, W. F. "Stable Transformation by Electroporation and Root Formation from Transformed Callus." *Proc. Natl. Acad. Sci. USA* 84:3962–3966.

DeBlaere, R. et al., 1987. "Vectors for Cloning in Plant Cells." *Methods Enzymol.* 153:277–305.

Faccioti, D., O'Neal, J. K., Lee, S. and Shewmaker, C. K., 1985. "Light-inducible Expression of A Chimeric Gene in Soybean Tissue Transformed with Agrobacterium." *Bio/Technology* 3:241–246.

Fraley, R. T., Rogers, S. G., Horsch, R. B., Eichholtz, D. A., Flick, J. S., Fink, C. L., Hoffman, N. L. and Sanders, P. R., 1985. "The SEV System: A New Disarmed Ti Plasmid Vector System for Plant Transformation." *BiO/Technology* 3:629–635.

Fry, J., Barnason, A. and Horsch, R. B., 1987. "Transformation of *Brassica napus* with *Agrobacterium tumefaciens* based vectors." *Plant Cell Reports* 6:321–325.

Gamborg, O. L., Miller, R. A. and Ojina, K., 1968. "Nutrient Requirements of Suspension Cultures of Soybean Root Cells." *Exp. Cell Res.* 50: 152–158.

Ghazi, T. D., Cheema, H. V. and Nabors, M. W., 1986. "Somatic embryogenesis and Plant Regeneration from Embryogenic Callus of Soybean, *Glycine max* L."*Plant Cell Reports* 5:452–456.

Jefferson, R. A., Burgess, S. M. and Hirsch, D., 1986. "β-glucuronidase from *E. coli* as a gene fusion marker." *Proc. Natl. Acad. Sci. USA.* 83:8447–8451.

Hammat, N. and Davey, M. R., 1987. "Somatic Embryogenesis and Plant Regeneration from Cultured Zygotic Embryos of Soybean (*Glycine max.* L. Merri.). *J. Plant Physiol.* 128:219–226.

Horsch, R. B. Fry, J. E. Hoffmann, N. L., Eichholtz, D., Rogers, S. G. and Fraley, R. T., 1985. "A Simple and General Method for Transferring Genes into Plants." *Science* 227:1229–1231.

Lin, W., Odell, J. T. and Schreiner, R. M., 1987. "Soybean Protoplast Culture and Direct Gene Uptake and Expression by Cultured Soybean Protoplasts."*Plant Physiol.* 84:856–861.

Lazzeri, P. A., Hildebrand, D. F. and Collins, G. B., 1985. "A Procedure for Plant Regeneration from Immature Cotyledon Tissue of Soybean."*Plant Mol. Biol. Rep.* 5:160–167.

McDonnell, R. E., Clark, R. D., Smith, W. A. and Hinchee, M. A., 1987. "A Simplified Method for the Detection of Neomycin Phosphotransferase II Activity in Transformed Plant Tissues." *Plant Mol. Biol. Rep.* 5:380–386.

Michelmore, R., Marsh, E., Seely, S. and Landry, B., 1987. Transformation of Lettuce (*lactuca sativa*) mediated by *Agrobacterium tumefaciens*."*Plant Cell Reports* 6:439–443.

Murashige, T. and Skoog, F., 1962. "A Revised Medium for Rapid Growth and Bioassays with Tobacco Tissue Cultures." *Physiol. Plant.* 15:473–497.

Owens, L. D. and Cress, D. E., 1985. "Genotypic Variability of Soybean Response to Agrobacterium Strains harboring the Ti or Ri Plasmids."*Plant Physiol.* 77:87–94.

Ranch, J. P., Oglesby, L. and Zielinski, A. C., 1985. "Plant Regeneration from Embryo-derived Tissue Cultures of Soybeans." *In Vitro Cell. & Dev. Biol.* 21:653–658.

Rhodes, C. A., Piece, D. A. Metler, I. J. Mascarenhas, D. and Detmer, J. J., 1988. "Genetically Transformed Maize Plants from Protoplats." *Science* 240:204–207.

Rogers, S. G., et al., 1987a. "Improved Vectors for Plant Transformation: Expression Cassette Vectors and New Selectable Markers." *Methods Enzymol.* 153:253–277.

Rogers, S. G., Klee, H. J., Horsch, R. B. and Fraley, R. T., 1987b. "Improved Vectors for Plant Transformation: Expression Cassette Vectors and New Selectable Markers." *Methods in Enzymology* 153:253–277.

Rogers, S. G. et al., 1986. "Gene Transfer in Plants: Production of Transformed Plants Using Ti Plasmid Vectors." *Methods Enzymol.* 118:627–640.

Rogers, S. G. and Klee, H. J., 1987b. "Pathways to Plant Genetic Manipulation Employing Agrobacterium."*Plant Gene Research—Plant DNA Infectious Agents,* Springer-Verlag Wien, New York.

Sanders, P. R., Winter, J. A., Barnason, A. R., Rogers, S. G. and Fraley, R. T., 1987. "Comparison of Cauliflower Mosaic Virus 35S and Nopaline Synthase Promoters in Transgenic Plants." *Nucleic Acids Research* 15:1543–1558.

Schenk, R. U. and Hildebrandt, A. C., 1972. "Medium and Techniques for Induction and Growth of Monocotyledonous and Dictoyledonous Plant Cell Cultures." *Can. J. Bot.* 50:199–204.

Wang, L., Yin, G., Luo, J., Lei, B., Wang, T., Yao, Z., Li, X., Shao, Q., Jiang, X. and Zhou, Z., 1983. "Proceedings First Intern. Symp. Soybean in Tropical and Subtropical Countries.

Wright, M. S., Koehler, S. M., Hinchee, M. A. and Carnes, M. G., 1986. Plant Regeneration by Organogenesis in *Glycine max.*" *Plant Cell Reports* 5:150–154.

Wright, M. S., Ward, D. V., Hinchee, M. A., Carnes, M. G. and Kaufman, R. J., 1987. "Regeneration of Soybean (*Glycine max* L. Merr.) from Cultured Primary Leaf Tissue." *Plant Cell Reports* 6: 83–89.

We claim:

1. A soybean plant comprising a chimeric gene and associated DNA resulting from an *Agrobacterium tumefaciens*-mediated transformation, said chimetic gene capable of conferring kanamycin resistance to said soybean plant, produced by the method which comprises:

(a) preparing a cotyledon explant from a soybean seedling by:
(i) removing the hypocotyl region by cutting just below the cotyledonary node,
(ii) separating the two cotyledons at the cotyledonary node, and
(iii) removing the epicotyl from the cotyledon to which it remains attached, (b) inserting a chimeric gene into the explant of part (a) by inoculation and co-cultivation of the explant with a disarmed *Agrobacterium tumefaciens* vector containing said chimeric gene;

(c) selecting transformed explant tissue, and (d) regenerating a differentiated transformed plant from the transformed explant tissue of part (c).

2. A seed produced from the plant of claim 1.

* * * * *